US012205033B2

(12) United States Patent
Song et al.

(10) Patent No.: US 12,205,033 B2
(45) Date of Patent: Jan. 21, 2025

(54) WEAKLY SUPERVISED LEARNING WITH WHOLE SLIDE IMAGES

(71) Applicants: NantOmics, LLC, Culver City, CA (US); NantHealth, Inc., Culver City, CA (US)

(72) Inventors: Bing Song, La Canada, CA (US); Mustafa Jaber, Los Angeles, CA (US); Liudmila Beziaeva, Culver City, CA (US); Shahrooz Rabizadeh, Los Angeles, CA (US)

(73) Assignees: NantOmics, LLC, Culver City, CA (US); NantHealth, Inc., Culver City, CA (US)

( * ) Notice: Subject to any disclaimer, the term of this patent is extended or adjusted under 35 U.S.C. 154(b) by 0 days.

(21) Appl. No.: 18/616,130

(22) Filed: Mar. 25, 2024

(65) Prior Publication Data

US 2024/0232629 A1 Jul. 11, 2024

Related U.S. Application Data

(63) Continuation of application No. 17/605,224, filed as application No. PCT/US2020/021919 on Mar. 10, 2020, now Pat. No. 11,954,596.

(Continued)

(51) Int. Cl.
*G06V 10/82* (2022.01)
*G06N 3/08* (2023.01)
(Continued)

(52) U.S. Cl.
CPC .............. *G06N 3/08* (2013.01); *G06T 7/0014* (2013.01); *G06T 7/194* (2017.01); *G06V 10/764* (2022.01);
(Continued)

(58) Field of Classification Search
CPC ..... G06T 7/194; G06T 7/0014; G06V 20/695; G06V 10/82; G06V 10/764
See application file for complete search history.

(56) References Cited

U.S. PATENT DOCUMENTS

| 9,430,829 B2 | 8/2016 | Madabhushi et al. |
| 10,049,770 B2 | 8/2018 | Madabhushi et al. |

(Continued)

OTHER PUBLICATIONS

International Search Report and Written Opinion issued in International Application No. PCT/US2020/021919 dated Jun. 29, 2020, 9 pages.

(Continued)

*Primary Examiner* — Sam Bhattacharya
(74) *Attorney, Agent, or Firm* — Maschoff Brennan; Andrew A. Noble

(57) ABSTRACT

Techniques are provided for determining classifications based on WSIs. A varied-size feature map is generated for each training WSI by generating a grid of patches for the training WSI, segmenting the training WSI into tissue and non-tissue areas, and converting patches comprising the tissue areas into tensors. Bounding boxes are generated based on the patches comprising tissue areas and segmented into feature map patches. A fixed-size feature map is generated based on a subset of the feature map patches. A classifier model is trained to process fixed-size feature maps corresponding to the training WSIs such that, for each fixed-size feature map, the classifier model is operable to assign a WSI-level tissue or cell morphology classification or regression based on the tensors. A classification engine is configured to use the trained classifier model to determine a WSI-level tissue or cell morphology classification or regression for a test WSI.

28 Claims, 13 Drawing Sheets

Related U.S. Application Data

(60) Provisional application No. 62/838,839, filed on Apr. 25, 2019.

(51) Int. Cl.

| | | |
|---|---|---|
| *G06T 7/00* | (2017.01) | |
| *G06T 7/194* | (2017.01) | |
| *G06V 10/764* | (2022.01) | |
| *G06V 10/766* | (2022.01) | |
| *G06V 10/77* | (2022.01) | |
| *G06V 10/774* | (2022.01) | |
| *G06V 20/69* | (2022.01) | |
| *G16H 10/40* | (2018.01) | |
| *G16H 30/40* | (2018.01) | |

(52) U.S. Cl.
CPC ........ *G06V 10/766* (2022.01); *G06V 10/7715* (2022.01); *G06V 10/774* (2022.01); *G06V 10/7747* (2022.01); *G06V 10/82* (2022.01); *G06V 20/695* (2022.01); *G06V 20/698* (2022.01); *G16H 10/40* (2018.01); *G16H 30/40* (2018.01); *G06T 2207/10024* (2013.01); *G06T 2207/20021* (2013.01); *G06T 2207/20081* (2013.01); *G06T 2207/20084* (2013.01); *G06T 2207/30096* (2013.01)

(56) References Cited

U.S. PATENT DOCUMENTS

| | | |
|---|---|---|
| 11,954,596 B2 | 4/2024 | Song et al. |
| 2014/0233826 A1 | 8/2014 | Agaian et al. |
| 2016/0307305 A1 | 10/2016 | Madabhushi et al. |
| 2019/0080795 A1 | 3/2019 | Sanghavi et al. |
| 2021/0166785 A1 | 6/2021 | Yip et al. |

OTHER PUBLICATIONS

International Preliminary Report on Patentability issued in International Application No. PCT/US2020/021919 dated Nov. 4, 2021, 6 pages.

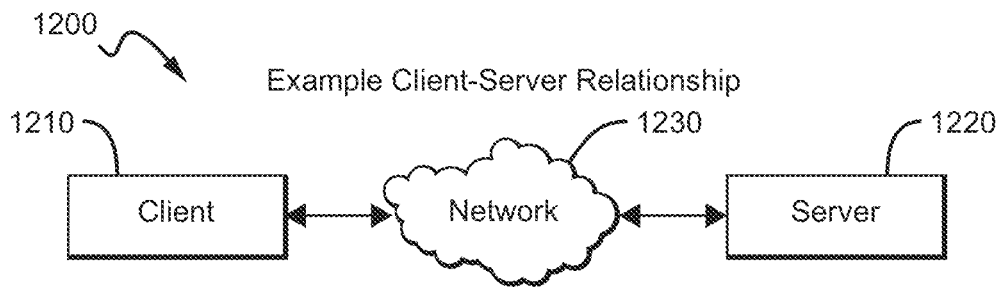

- obtain and automatically upload training WSIs
- optimally select a training dataset from the training WSIs
- obtain and automatically upload test WSI slide image
- receive tissue and/or cell morphology classification or regression result

- obtain plurality of training WSIs;
- generate varied-size feature map for each of the plurality of training WSIs by generating grid of patches for the training WSI, segmenting the training WSI into tissue and non-tissue areas, and converting patches comprising tissue areas into tensors;
- generate at least one bounding box based on the patches comprising tissue areas;
- segment the at least one bounding box into feature map patches;
- generate fixed-size feature map based on subset of the feature map patches;
- configure classifier model to process fixed-size feature maps corresponding to training WSIs such that, for each fixed-size feature map, the classifier model is operable to assign a WSI-level tissue and/or cell morphology classification or regression based on the tensors;
- train classifier model using the fixed-size feature maps corresponding to the plurality of training WSIs;
- configure molecular classification engine to use trained classifier model to determine WSI-level molecular classification or regression for test WSI

FIG. 12

WEAKLY SUPERVISED LEARNING WITH WHOLE SLIDE IMAGES

CROSS REFERENCE TO RELATED APPLICATIONS

This application is a continuation application of U.S. Application Ser. No. 17/605,224 filed on Oct. 20, 2021, which is a national phase application of International Application No. PCT/US2020/021919 filed on Mar. 10, 2020, which claims priority to U.S. Provisional Application No. 62/838,839 filed on Apr. 25, 2019. The entire contents of these applications are hereby incorporated herein by reference.

TECHNICAL FIELD

This disclosure relates generally to imaging for pathology applications, and more specifically to using whole slide images for tissue or cell morphology classification.

BACKGROUND

Hematoxylin and eosin (H&E)-stained biopsy slides are routinely collected during pathological examination and are often digitally recorded as whole slide images (WSIs). In general, slide imaging (e.g., whole slide imaging) refers to the scanning of conventional glass slides to produce digital slides and is used by pathologists for diagnostic, educational and research purposes.

Machine learning approaches can extract knowledge from WSIs beyond that of which a human is capable, as evidenced by the many computer-assisted diagnosis (CAD) software solutions created to augment pathological inspection workflows. Further, image-based tissue or cell morphology classification (e.g., type/subtype of cancer, grade of cancer, percentage of true lymphocytes, etc.) can be achieved by using WSIs as input to machine learning models. For example, deep learning methods are an emerging set of influential machine learning technologies well suited to these image-based tissue or cell morphology classification tasks. Recent advances in both computational power and convolutional network architectures have greatly increased the applicability of these techniques for several new domains in biology including—omics analysis, biomedical signal processing and biomedical imaging.

One drawback of deep learning methods for pathology applications is that machine learning models have typically required using thousands or tens of thousands of images for training. However, due to the lack of patient data sharing, and regulations preventing the same, it is often not practical or impossible to acquire such large amounts of previously classified WSIs for training purposes. Therefore, until now "weakly supervised" deep learning models that can trained for determining image-based tissue or cell morphology classifications based on a limited amount of training whole slide images has been seen only as an area of ongoing research.

SUMMARY

Systems, methods, and articles of manufacture for determining image-based classifications based on training whole slide images (WSIs) (e.g., of hematoxylin and eosin (H&E)-stained biopsy tissue sections) are described herein. Particularly, a weakly supervised classifier model may be trained using a limited amount (~100 s) of labeled WSIs and subsequently used determine a tissue and/or cell morphology classification or regression for a test WSI (e.g., to classify the test WSI based on a type/subtype of cancer, cancer grade, percentage of true lymphocytes, etc.). The WSI-level tissue and/or cell morphology classification may capture morphology structures from several microns to several millimeters in size. As such, advanced machine learning methods can approximate tissue and/or cell morphology classifications or regressions determined by pathologists using available amounts of routinely collected WSIs, and thus may increase prognostic capabilities.

In one embodiment, a plurality of training WSIs, e.g., labeled hematoxylin and eosin (H&E)-stained whole slide images each corresponding to a patient, is obtained. The plurality of training WSIs may comprise less than one thousand pathology slide images, each corresponding to an WSI-level label indicating at least one of a type of cancer, a cancer grade, or a regression such as a percentage of tumor-infiltrating lymphocytes, RNA expression, mutation burden, allele frequency, etc. Each of the plurality of training WSIs may correspond to a different patient. A varied-size feature map is generated for each of the plurality of training WSIs by generating a grid of patches for the training WSI, segmenting the training WSI into tissue and non-tissue areas, and converting patches comprising the tissue areas into tensors, e.g., multidimensional descriptive vectors comprising RGB components. An RGB component of the image patch may be converted into a feature vector, e.g., a 512-feature vector for a resnet34 deep-learning neural network. However, the feature vector is not limited to a 512-feature vector or a particular deep learning model. At least one bounding box is generated based on the patches comprising the tissue areas. The at least one bounding box is segmented into feature map patches. A fixed-size feature map is generated based on at least a subset of the feature map patches, which may be randomly selected and/or arranged randomly within the fixed-size feature map. The fixed-size feature map may comprise one of a (256, 256, 512) or (224, 224, 512) feature map. A classifier model is configured to process fixed-size feature maps corresponding to the training WSIs such that, for each fixed-size feature map, the classifier model is operable to assign a WSI-level tissue or cell morphology classification or regression based on the tensors. The classifier model is trained using the fixed-size feature maps corresponding to the plurality of training WSIs, and a classification engine is configured to use the trained classifier model to determine a WSI-level tissue or cell morphology classification or regression for a test WSI.

In some embodiments, patches of the grid of patches determined to comprise non-tissue areas are converted into tensors comprising white feature components.

In some embodiments, the grid of patches may be filtered for a minimum color variance, and each patch determined to be empty space or background may be eliminated from further processing based on the filtering.

In some embodiments, each of the feature map patches may comprise a fixed-size patch, e.g., one of a 1.6 mm×1.6 mm or 3.2 mm×3.2 mm fixed-size patch.

In some embodiments, the subset of the feature map patches also may be randomly selected to define cancer-enriched areas or to summarize tumor content within a training WSI.

In some embodiments, the classifier model may comprise a modified resnet34 deep-learning neural network, a two-layer convolutional deep-learning neural network or at least one of an Inception-v3, resnet34, resnet152, densenet169, densenet201 or other deep-learning neural network.

In some embodiments, a test WSI is obtained. A varied-size feature map is generated for the test WSI by generating a grid of patches for the test WSI, segmenting the test WSI into tissue and non-tissue areas, and converting patches comprising the tissue areas into tensors. At least one bounding box is generated based on the patches comprising the tissue areas. The at least one bounding box is segmented into feature map patches. A fixed-size feature map is generated based on at least a subset of the feature map patches, and the fixed-size feature map is processed using the trained classifier model, wherein the trained classifier model is operable to determine a WSI-level tissue or cell morphology classification or regression for the test WSI based on the fixed-size feature map.

Various objects, features, aspects and advantages of the inventive subject matter will become more apparent from the following specification, along with the accompanying drawings in which like numerals represent like components.

BRIEF DESCRIPTION OF THE DRAWINGS

FIG. 12 illustrates a block diagram of an exemplary client-server relationship that can be used for implementing one or more aspects of the various embodiments.

Figure 1:
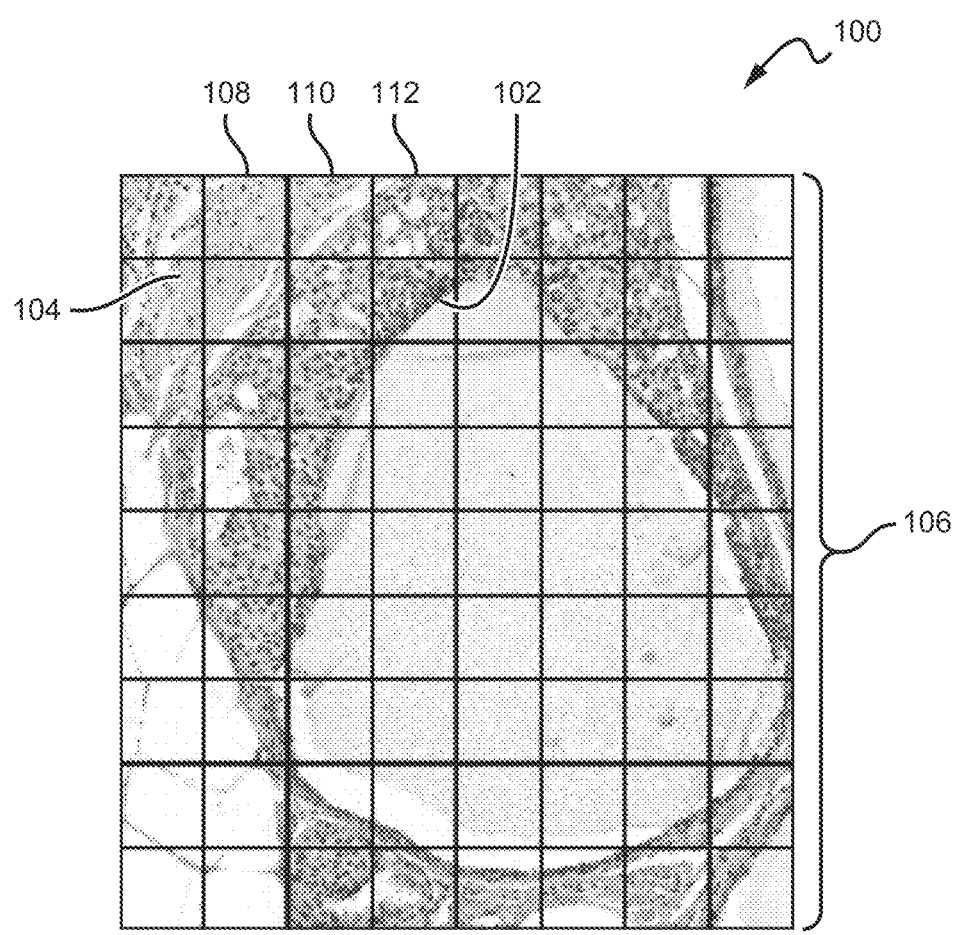
FIG. 1 illustrates a graphical representation of a pathology slide image in accordance with an embodiment.

While the invention is described with reference to the above drawings, the drawings are intended to be illustrative, and other embodiments are consistent with the spirit, and within the scope, of the invention.

DETAILED DESCRIPTION

The various embodiments now will be described more fully hereinafter with reference to the accompanying drawings, which form a part hereof, and which show, by way of illustration, specific examples of practicing the embodiments. This specification may, however, be embodied in many different forms and should not be construed as being limited to the embodiments set forth herein; rather, these embodiments are provided so that this specification will be thorough and complete, and will fully convey the scope of the invention to those skilled in the art. Among other things, this specification may be embodied as methods or devices. Accordingly, any of the various embodiments herein may take the form of an entirely hardware embodiment, an entirely software embodiment or an embodiment combining software and hardware aspects. The following specification is, therefore, not to be taken in a limiting sense.

Throughout the specification and claims, the following terms take the meanings explicitly associated herein, unless the context clearly dictates otherwise:

The phrase "in one embodiment" as used herein does not necessarily refer to the same embodiment, though it may. Thus, as described below, various embodiments of the invention may be readily combined, without departing from the scope or spirit of the invention.

As used herein, the term "or" is an inclusive "or" operator and is equivalent to the term "and/or," unless the context clearly dictates otherwise.

The term "based on" is not exclusive and allows for being based on additional factors not described, unless the context clearly dictates otherwise.

As used herein, and unless the context dictates otherwise, the term "coupled to" is intended to include both direct coupling (in which two elements that are coupled to each other contact each other) and indirect coupling (in which at least one additional element is located between the two elements). Therefore, the terms "coupled to" and "coupled with" are used synonymously. Within the context of a networked environment where two or more components or devices are able to exchange data, the terms "coupled to" and "coupled with" are also used to mean "communicatively coupled with", possibly via one or more intermediary devices.

In addition, throughout the specification, the meaning of "a", "an", and "the" includes plural references, and the meaning of "in" includes "in" and "on".

Although some of the various embodiments presented herein constitute a single combination of inventive elements, it should be appreciated that the inventive subject matter is considered to include all possible combinations of the disclosed elements. As such, if one embodiment comprises elements A, B, and C, and another embodiment comprises elements B and D, then the inventive subject matter is also considered to include other remaining combinations of A, B, C, or D, even if not explicitly discussed herein. Further, the transitional term "comprising" means to have as parts or members, or to be those parts or members. As used herein, the transitional term "comprising" is inclusive or open-ended and does not exclude additional, unrecited elements or method steps.

Throughout the following discussion, numerous references will be made regarding servers, services, interfaces, engines, modules, clients, peers, portals, platforms, or other systems formed from computing devices. It should be appreciated that the use of such terms is deemed to represent one or more computing devices having at least one processor (e.g., ASIC, FPGA, DSP, x86, ARM, ColdFire, GPU, multi-core processors, etc.) configured to execute software instructions stored on a computer readable tangible, non-transitory medium (e.g., hard drive, solid state drive, RAM, flash, ROM, etc.). For example, a server can include one or more computers operating as a web server, database server, or other type of computer server in a manner to fulfill described roles, responsibilities, or functions. One should further appreciate the disclosed computer-based algorithms, processes, methods, or other types of instruction sets can be embodied as a computer program product comprising a non-transitory, tangible computer readable medium storing the instructions that cause a processor to execute the disclosed steps. The various servers, systems, databases, or interfaces can exchange data using standardized protocols or algorithms, possibly based on HTTP, HTTPS, AES, public-private key exchanges, web service APIs, known financial transaction protocols, or other electronic information exchanging methods. Data exchanges can be conducted over a packet-switched network, a circuit-switched network, the Internet, LAN, WAN, VPN, or other type of network.

As used in the description herein and throughout the claims that follow, when a system, engine, server, device, module, or other computing element is described as being configured to perform or execute functions on data in a memory, the meaning of "configured to" or "programmed to" is defined as one or more processors or cores of the computing element being programmed by a set of software instructions stored in the memory of the computing element to execute the set of functions on target data or data objects stored in the memory.

It should be noted that any language directed to a computer should be read to include any suitable combination of computing devices, including servers, interfaces, systems, databases, agents, peers, engines, controllers, modules, or other types of computing devices operating individually or collectively. One should appreciate the computing devices comprise a processor configured to execute software instructions stored on a tangible, non-transitory computer readable storage medium (e.g., hard drive, FPGA, PLA, solid state drive, RAM, flash, ROM, etc.). The software instructions configure or program the computing device to provide the roles, responsibilities, or other functionality as discussed below with respect to the disclosed apparatus. Further, the disclosed technologies can be embodied as a computer program product that includes a non-transitory computer readable medium storing the software instructions that causes a processor to execute the disclosed steps associated with implementations of computer-based algorithms, processes, methods, or other instructions. In some embodiments, the various servers, systems, databases, or interfaces exchange data using standardized protocols or algorithms, possibly based on HTTP, HTTPS, AES, public-private key exchanges, web service APIs, known financial transaction protocols, or other electronic information exchanging methods. Data exchanges among devices can be conducted over a packet-switched network, the Internet, LAN, WAN, VPN, or other type of packet switched network; a circuit switched network; cell switched network; or other type of network.

The focus of the disclosed inventive subject matter is to enable construction or configuration of a computing device to operate on vast quantities of digital data, beyond the capabilities of a human for purposes including determining a tissue or cell morphology classification or regression for a digitally recorded pathology slide image.

One should appreciate that the disclosed techniques provide many advantageous technical effects including improving the scope, accuracy, compactness, efficiency, and speed of determining a tissue or cell morphology classification or regression for a digitally recorded pathology slide image. It should also be appreciated that the following specification is not intended as an extensive overview, and as such, concepts may be simplified in the interests of clarity and brevity.

Systems, methods, and articles of manufacture for determining tissue or cell morphology classifications or regressions based on whole slide images (WSIs), e.g., whole-slide images of hematoxylin and eosin (H&E)-stained biopsy tissue sections, are described herein. The various embodiments provide for a classifier model to be trained to determine a WSI-level tissue and/or cell morphology classification or regression using deep learning methods based on a limited set of training pathology slide images. Thus, the limited number of available whole slide images due to a lack of patient data sharing, and regulations preventing the same, can be overcome by methods that require a relatively limited amount (~100 s) of labeled whole slide images for training purposes. The various embodiments herein do not require detailed annotation of WSIs. Further, the embodiments herein overcome various storage and processing challenges of using typically very large whole slide images (e.g., 100,000×100,000 pixels or more) for deep-learning applications due to techniques for randomly generating fixed-size maps that reduce the size of the training dataset.

FIG. 1 illustrates a graphical representation of a pathology slide image in accordance with an embodiment of the present invention. A pathology slide image (SI) 100, e.g., a whole-slide image, may be generated when a pathologist wishes to look at a biopsy of a suspected cancer or make other medical diagnoses. Typically, a pathology whole-slide image such as SI 100 may include more than two million cells. Thus, a hematoxylin and eosin stain ("H&E stain" or "HE stain"), may be used for distinguishing the various structures within the whole slide pathology image. As shown, hematoxylin is a dark blue or violet stain that binds to various tissue/cellular regions 102 (i.e., basophilic substances such as DNA and RNA), while eosin is a red or pink stain that binds to acidophilic substances including cytoplasmic filaments in muscle cells, intracellular membranes, and extracellular fibers such as, for example, plasma region 104. In an embodiment, a grid of patches 106, e.g., comprising patches 108, 110, and 112, may be generated for SI 100 to segment SI 100 into majority tissue and non-tissue areas.

Figure 2:
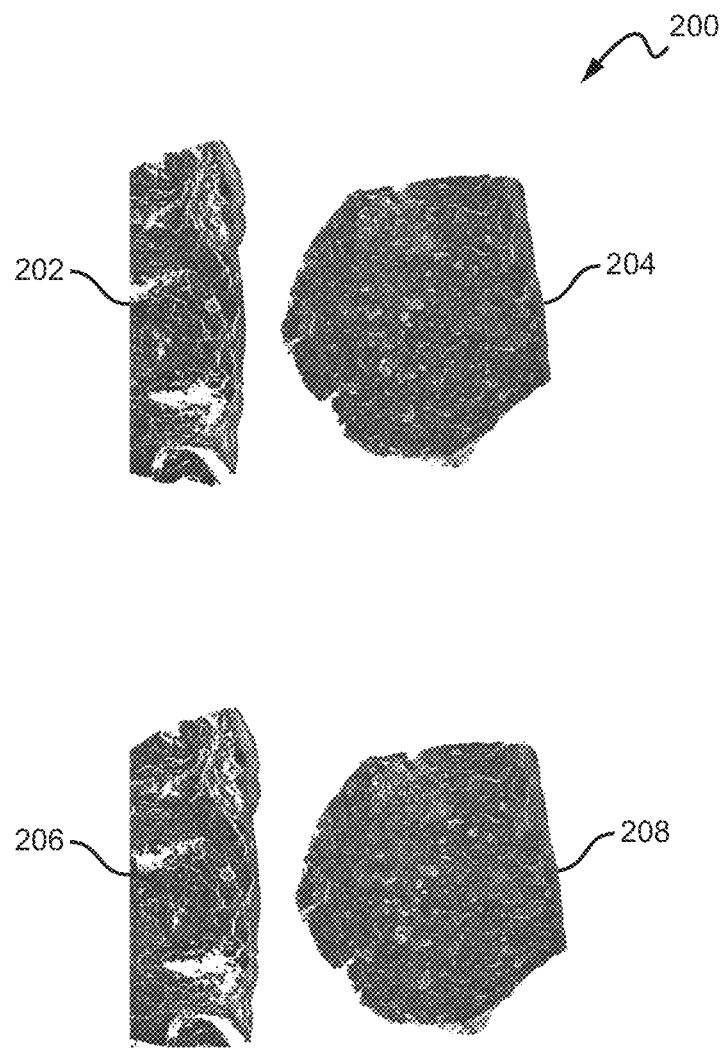
FIG. 2 illustrates a graphical representation of a pathology slide image having a binary tissue mask overlay in accordance with an embodiment.

FIG. 2 illustrates a graphical representation of a pathology slide image having a binary tissue mask overlay in accordance with an embodiment. After the grid of patches 106 is generated, one or more tissue bounding boxes, e.g., can be generated using a binary tissue mask overlay 200. In an embodiment, binary tissue mask overlay 200 masks the non-tissue areas of SI 100 and defines the tissue areas, e.g., tissue areas 202, 204, 206, and 208. In an embodiment, patches of the grid of patches 106 comprising the tissue areas, e.g., patches within tissue areas 202, 204, 206, and 208, may be converted into tensors, e.g., multidimensional descriptive vectors. For example, an RGB portion of the image patch may be converted into a 512-feature vector for a resnet34 deep-learning neural network. However, the feature vector is not limited to 512 features or a particular deep learning model. In an embodiment, patches of the grid of patches 106 determined to comprise non-tissue areas may be converted into tensors comprising white feature components. In addition, or alternatively, the grid of patches 106 may be filtered for a minimum color variance, and each patch determined to be empty space or background may be eliminated from further processing based on the filtering.

Figure 3:
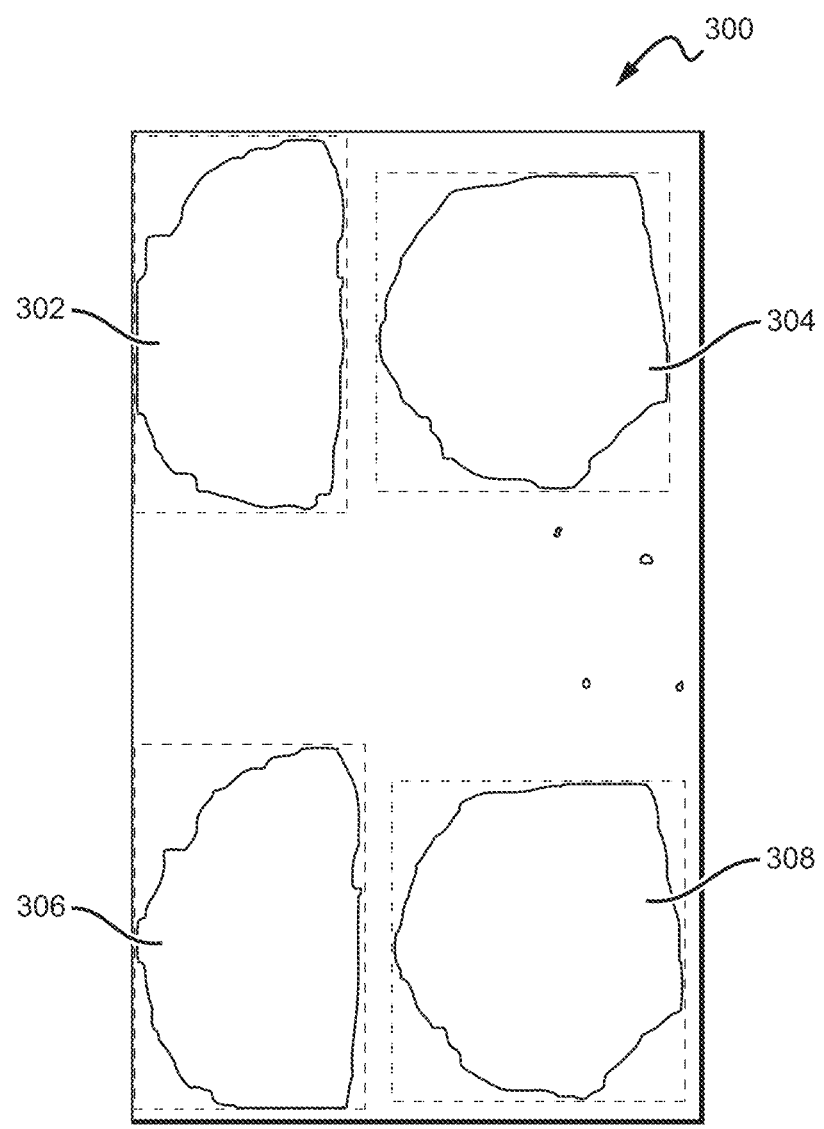
FIG. 3 illustrates a graphical representation of a pathology slide image having at least one bounding box based on patches comprising tissue areas in accordance with an embodiment.

FIG. 3 illustrates a graphical representation of a pathology slide image having at least one bounding box based on patches comprising tissue areas in accordance with an embodiment. As shown overlay image 300, the tissue areas, e.g., tissue areas 202, 204, 206, and 208, can determine the locations of one or more bounding boxes. For example, overlay image 300 includes bounding boxes 302, 304, 306, and 308 generated to comprise tissue areas 202, 204, 206, and 208, respectively. In an embodiment, each bounding box, e.g., each of bounding boxes 302, 304, 306, and 308, is segmented into feature map patches. For example, each bounding box may be segmented into one or more fixed-size 1.6 mm×1.6 mm patches, in which each patch may include about 100,000 cells. Further, the feature map patches may be converted into tensors comprising multidimensional RGB components, e.g., (16, 16, N) tensors, where N is a feature vector size. For example, in a resnet34 deep-learning neural network, N=512. Alternatively, each bounding box may be segmented into one or more 3.2 mm×3.2 mm feature map patches that are converted into tensors comprising multidimensional RGB components, e.g., (32, 32, N) tensors.

Figure 4:
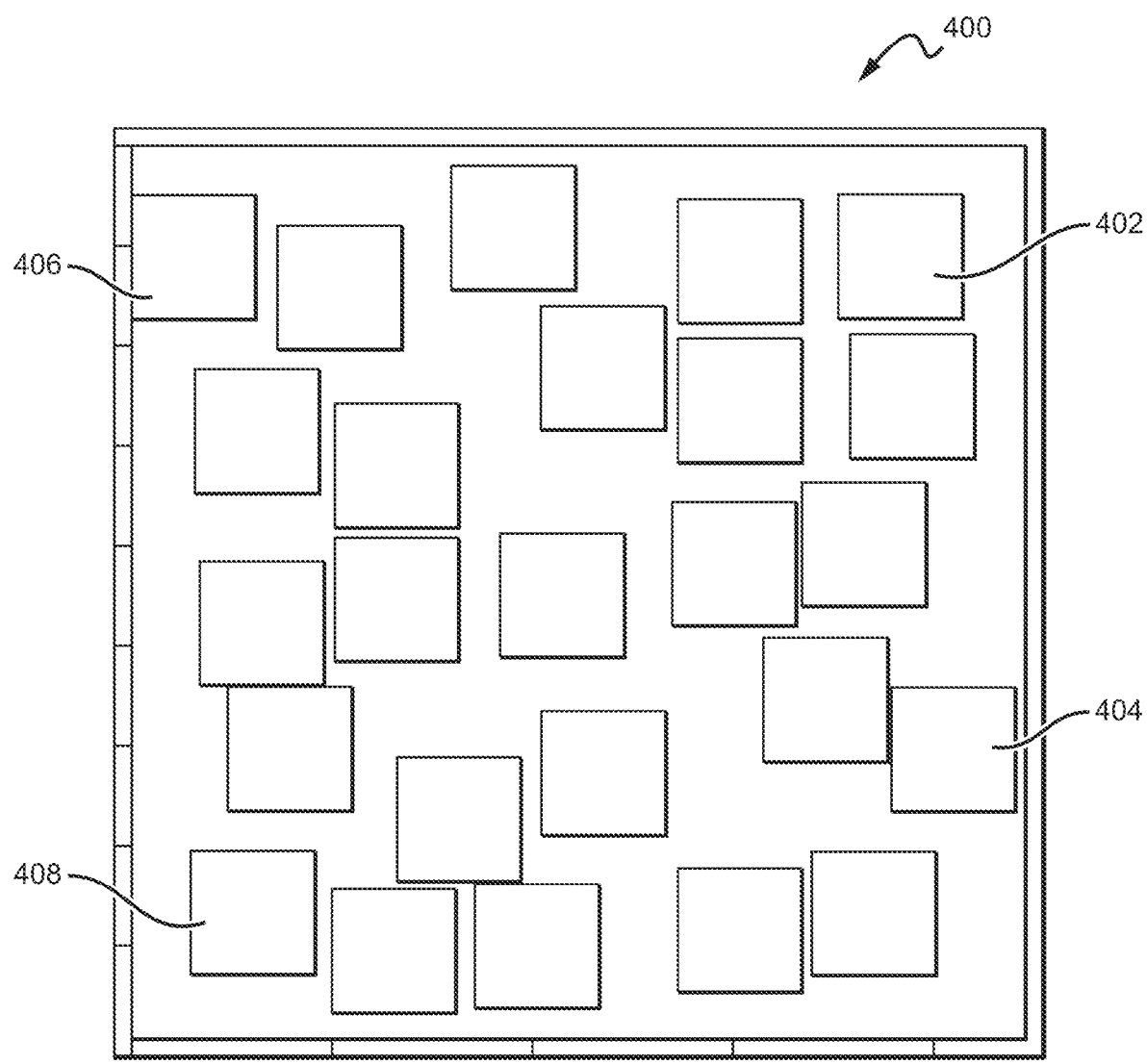
FIG. 4 illustrates a graphical representation of a fixed-size feature map in accordance with an embodiment.

FIG. 4 illustrates a graphical representation of a fixed-size feature map in accordance with an embodiment. Fixed-size feature map 400 is generated based on bounding boxes 302, 304, 306, and 308. For example, fixed-size feature map 400 may be one of a (256, 256, 512) feature map (including RGB), a (224, 224, 512) feature map (including RGB) or another fixed size that may correspond to, e.g., a deep-learning classifier model fixed-size input. In an embodiment, fixed-size feature map 400 is generated based on at least a subset of the feature map patches, e.g., feature map patches 402, 404, 406, and 408, which may be randomly selected and/or arranged randomly within fixed-size feature map 400. Further, each time fixed-size feature map 400 is generated based on bounding boxes 302, 304, 306, and 308, the locations of the subset of the feature map patches may be different within the fixed-size feature map. In some embodiments, the subset of the feature map patches may be randomly selected to define cancer-enriched areas or to summarize tumor content within a training WSI.

Figure 5:
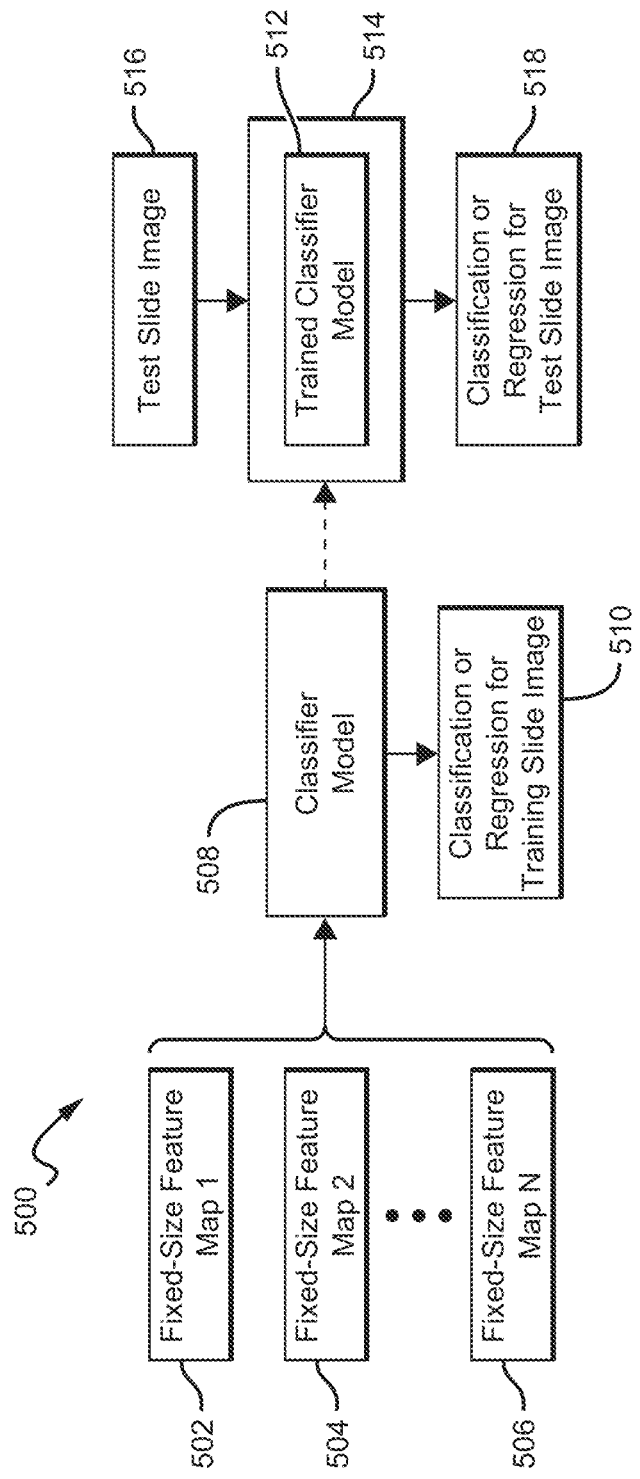
FIG. 5 illustrates a block diagram of example operations for determining tissue or cell morphology classifications or regressions based on whole slide images in accordance with an embodiment.

FIG. 5 illustrates a block diagram of example operations for determining tissue or cell morphology classifications or regressions based on whole slide images in accordance with an embodiment. In system 500, a deep learning neural network model trained using fixed-size feature maps that allows for the analysis of WSI characteristics, e.g., morphology structures from several microns to several millimeters in size. In an embodiment, a plurality of training WSIs (e.g., lung adeno and squamous carcinoma diagnostic whole-slide images obtained from TCGA, LUAD, or LUSC data sources) may be used to generate fixed-size feature maps, e.g., fixed-size feature maps 1-N 502, 504, 506, that reduce the size of the training dataset for further processing. For example, each of the plurality of training WSIs may correspond to a different patient. Fixed-size feature maps 1-N 502, 504, 506 may be (256, 256, 512) or (224, 224, 512) in size and may include randomly selected and/or randomly arranged feature map patches. For example, a varied-size feature map may be generated for each of the plurality of training WSIs by generating a grid of patches for the training WSI, segmenting the training WSI into tissue and non-tissue areas, and converting patches comprising the tissue areas into tensors, e.g., multidimensional descriptive vectors comprising RGB components. At least one bounding box may be generated based on the patches comprising the tissue areas and segmented into feature map patches. A fixed-size feature map for processing, e.g., each of fixed-size feature maps 1-N 502, 504, 506, may be generated based on at least a subset of the feature map patches, which may be randomly selected and/or arranged randomly within the fixed-size feature map.

Classifier model 508 may comprise at least one of an Inception-v3, resnet34, resnet152, densenet169, densenet201 or other deep-learning neural network. In one embodiment, a classifier model 508 comprises one of a modified Resnet or two-layer convnet configured to process fixed-size feature maps, e.g., fixed-size feature maps 1-N 502, 504, 506, corresponding to training WSIs such that, for each fixed-size feature map, the classifier model is operable to assign a WSI-level tissue and/or cell morphology classification or regression 510 for a training WSI based on the tensors. WSI-level tissue and/or cell morphology classification or regression 510 may be, for example, a binary prediction of a type/subtype of cancer, grade of cancer, percentage of true lymphocytes, etc. The WSI-level tissue and/or cell morphology classification may capture morphology structures from several microns to several millimeters in size. Classifier model 508 is trained using fixed-size feature maps, e.g., fixed-size feature maps 1-N 502, 504, 506, corresponding to a plurality of training WSIs, and classification engine 512 is configured to use trained classifier model 514 for a test WSI 516 to determine a WSI-level tissue and/or cell morphology classification or regression 518 (e.g., type/subtype of cancer, grade of cancer, percentage of true lymphocytes, etc.). In an embodiment, the WSI-level tissue and/or cell morphology classification may capture morphology structures from several microns to several millimeters in size.

Figure 6:
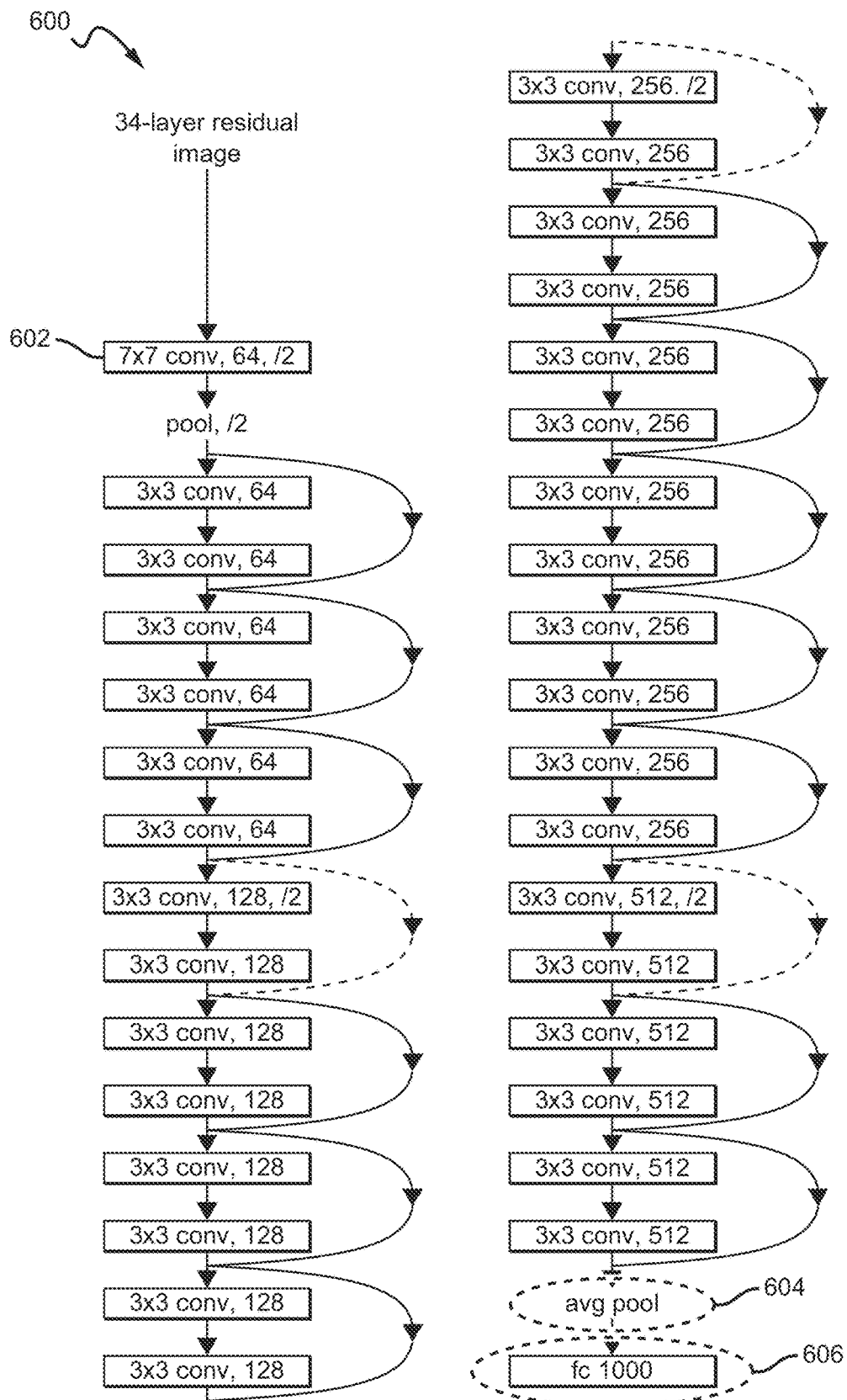
FIG. 6 illustrates a block diagram of a classifier model for determining tissue or cell morphology classifications or regressions based on whole slide images in accordance with an embodiment.

FIG. 6 illustrates a block diagram of a classifier model for determining tissue or cell morphology classifications or regressions based on whole slide images in accordance with an embodiment. Classifier model 600 illustrates a Resnet classifier model having (512, 64, 128, 256, 512) convolutional channels. In a Resnet classifier model modified, e.g., for a (224, 224, 512) fixed-size feature map input, a typical (3, 7, 7, 64, %) convolutional layer 602 may be replaced by a (512, 3, 3, 64, 1) convolutional layer, and a typical (7, 7) average pooling layer 604 may be replaced by a (14, 14) average pooling layer to compensate for the convolutional layer modification. In addition, a typical (512, 1000) fully connected layer 606 may be replaced by a (512, 2) fully connected layer, in which the two-channel output results in, e.g., a cancer or non-cancer classification.

Figure 7:
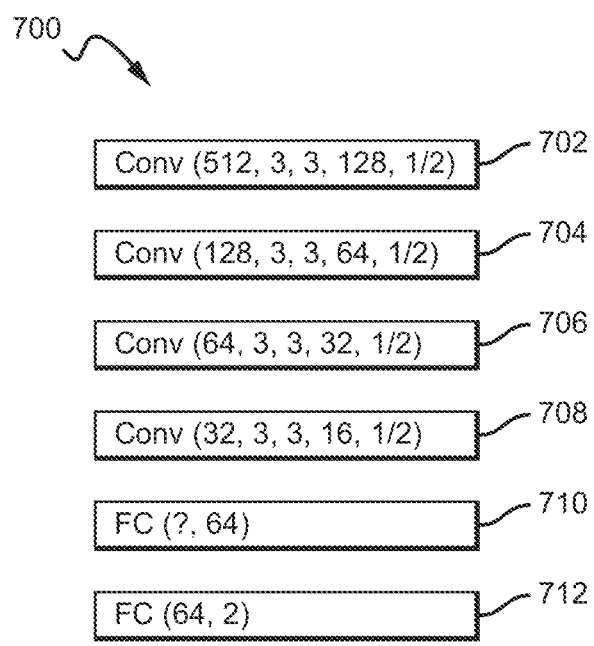
FIG. 7 illustrates a block diagram of a classifier model for determining tissue or cell morphology classifications or regressions based on whole slide images in accordance with an embodiment.

FIG. 7 illustrates a block diagram of a classifier model for determining tissue or cell morphology classifications or regressions based on whole slide images in accordance with an embodiment. Classifier model 700 illustrates a two-layer Convnet classifier model where each convolutional block comprises at least one of two convolutional layers, a Resnet basic layer and a Resnet bottleneck layer. For example, the convolutional layers, e.g., convolutional layers 702, 704, 706, 708, comprise (512, 256, 128, 64, 32) convolutional channels, and the one or more fully connected layers, e.g., fully connected layers 710 and 712, result in a two-channel classification output, e.g., indicating a cancer or non-cancer classification. Alternatively, for a regression output (e.g., a percentage of tumor-infiltrating lymphocytes, RNA expression, mutation burden, or allele frequency), the softmax+ cross entropy loss classifier portion of the model may be replaced with a square residual loss function.

Figure 8:
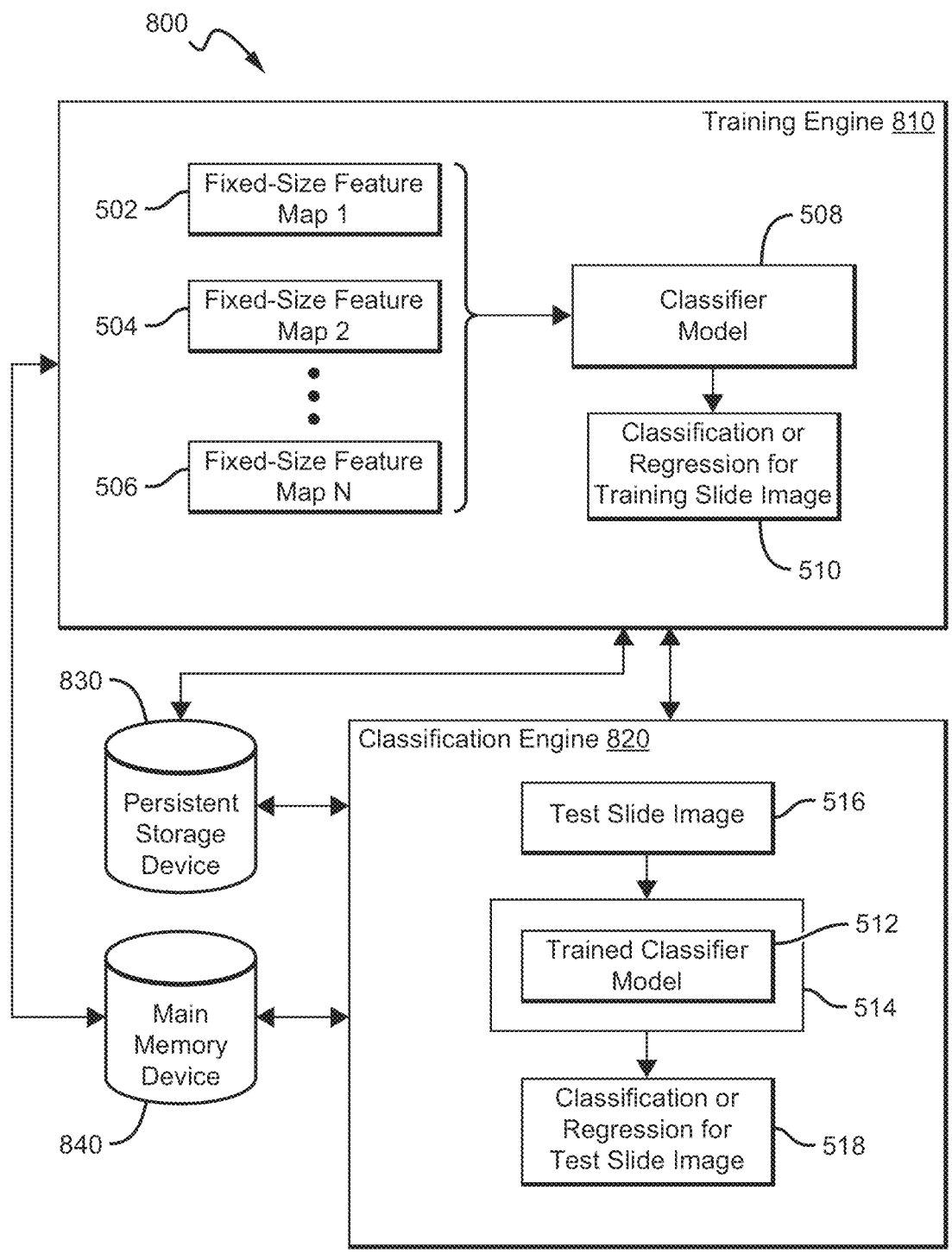
FIG. 8 illustrates a block diagram of a system for determining tissue or cell morphology classifications or regressions based on whole slide images in accordance with an embodiment.

FIG. 8 illustrates a block diagram of a system for determining tissue or cell morphology classifications or regressions based on whole slide images in accordance with an embodiment. In block diagram 800, elements for determining tissue and/or cell morphology classifications or regressions based on whole slide images include training engine 810, classification engine 820, persistent storage device 830, and main memory device 840. In an embodiment, training engine 810 may be configured to obtain fixed-size feature maps, e.g., fixed-size feature maps 1-N 502, 504, 506, from either one or both of persistent storage device 830 and main memory device 840. Training engine 810 may then configure and train classifier model 508, which may be stored in either one or both of persistent storage device 830 and main memory device 840, using the fixed-size feature maps, e.g., fixed-size feature maps 1-N 502, 504, 506, as training inputs. For example, training engine 810 may generate a varied-size feature map for each of a plurality of training WSIs by generating a grid of patches for the training WSI, segmenting the training WSI into tissue and non-tissue areas, and converting patches comprising the tissue areas into tensors, e.g., multidimensional descriptive vectors comprising RGB components. Training engine 810 may then generate at least one bounding box based on the patches comprising the tissue areas, segment the at least one bounding box into feature map patches, and generate each fixed-size feature map, e.g., fixed-size feature maps 1-N 502, 504, 506, based on at least a subset of the feature map patches, which may be randomly selected and/or arranged randomly within the fixed-size feature map. Training engine 310 may configure and train classifier model 508 to process the fixed-size feature maps 1-N 502, 504, 506 such that, for each training WSI, classifier model 508 is operable to assign a WSI-level tissue and/or cell morphology classification or regression 510 based on the tensors.

Training engine 810 may configure classification engine 820 to use trained classifier model 514 to determine a WSI-level tissue and/or cell morphology classification or regression based on a test WSI 516. For example, classification engine 820 may obtain test WSI 516 and generate a varied-size feature map for test WSI 516 by generating a grid of patches for the test WSI, segmenting the test WSI into tissue and non-tissue areas, and converting patches comprising the tissue areas into tensors. Classification engine 820 may generate at least one bounding box based on the patches comprising the tissue areas, segment the at least one bounding box into feature map patches, and generate a fixed-size feature map based on at least a subset of the feature map patches. Classification engine 820 may then process the fixed-size feature map using trained classifier model 514, where the trained classifier model is operable to determine a WSI-level tissue and/or cell morphology classification or regression 518 for test WSI 516 based on the fixed-size feature map.

It should be noted that the elements in FIG. 8, and the various functions attributed to each of the elements, while exemplary, are described as such solely for the purposes of ease of understanding. One skilled in the art will appreciate that one or more of the functions ascribed to the various elements may be performed by any one of the other elements, and/or by an element (not shown) configured to perform a combination of the various functions. Therefore, it should be noted that any language directed to a training engine 810, a classification engine 820, a persistent storage device 830, and a main memory device 840 should be read to include any suitable combination of computing devices, including servers, interfaces, systems, databases, agents, peers, engines, controllers, modules, or other types of computing devices operating individually or collectively to perform the functions ascribed to the various elements. Further, one skilled in the art will appreciate that one or more of the functions of the system of FIG. 8 described herein may be performed within the context of a client-server relationship, such as by one or more servers, one or more client devices (e.g., one or more user devices) and/or by a combination of one or more servers and client devices.

Figure 9:
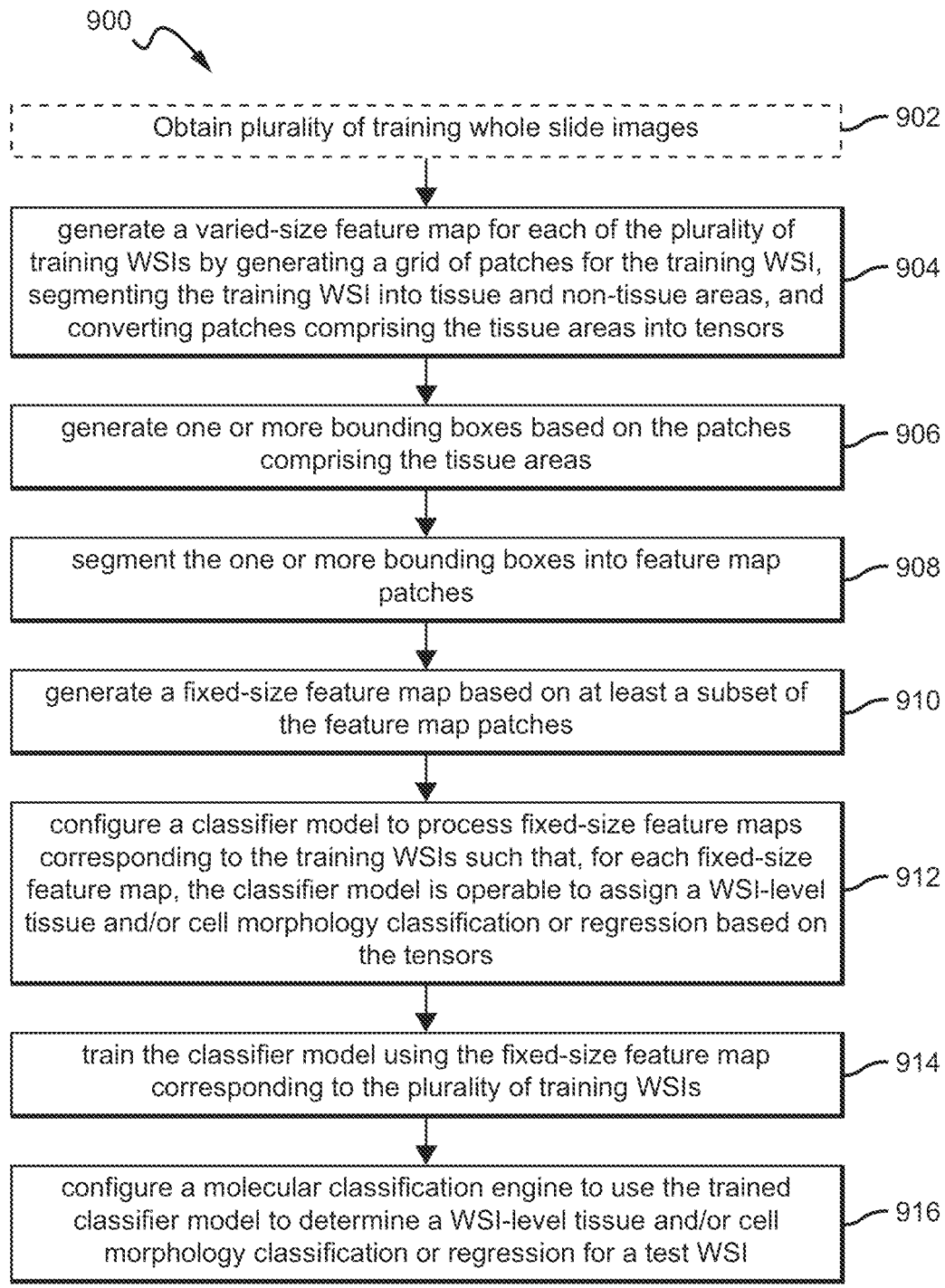
FIG. 9 illustrates a flow diagram of example operations for determining tissue or cell morphology classifications or regressions based on whole slide images in accordance with an embodiment.

FIG. 9 illustrates a flow diagram of example operations for determining tissue or cell morphology classifications or regressions based on whole slide images in accordance with an embodiment. In flow diagram 900, a plurality of training WSIs, e.g., training WSIs 1 to N 502, 504, 506, is obtained at step 902 and a varied-size feature map is generated for each of the plurality of training WSIs at step 904 by generating a grid of patches for the training WSI, segmenting the training WSI into tissue and non-tissue areas, and converting patches comprising the tissue areas into tensors. For example, an RGB component of the image patch may be converted into a 512-feature vector for a resnet34 deep-learning neural network. However, the feature vector is not limited to a 512-feature vector or a particular deep learning model. At step 906, at least one bounding box is generated based on the patches comprising the tissue areas, and the at least one bounding box is segmented into feature map patches at step 908. At step 910, a fixed-size feature map is generated based on at least a subset of the feature map patches, which may be randomly selected and/or arranged randomly within the fixed-size feature map. For example, the fixed-size feature map may comprise one of a (256, 256, 512) feature map or a (224, 224, 512) feature map. At step 912, a classifier model is configured to process fixed-size feature maps corresponding to the training WSIs such that, for each fixed-size feature map, the classifier model is operable to assign a WSI-level tissue and/or cell morphology classification or regression based on the tensors. At step 914, the classifier model is trained using the fixed-size feature maps corresponding to the plurality of training WSIs, and a classification engine is configured to use the trained classifier model to determine a WSI-level tissue and/or cell morphology classification or regression for a test WSI at step 916.

Figure 10:
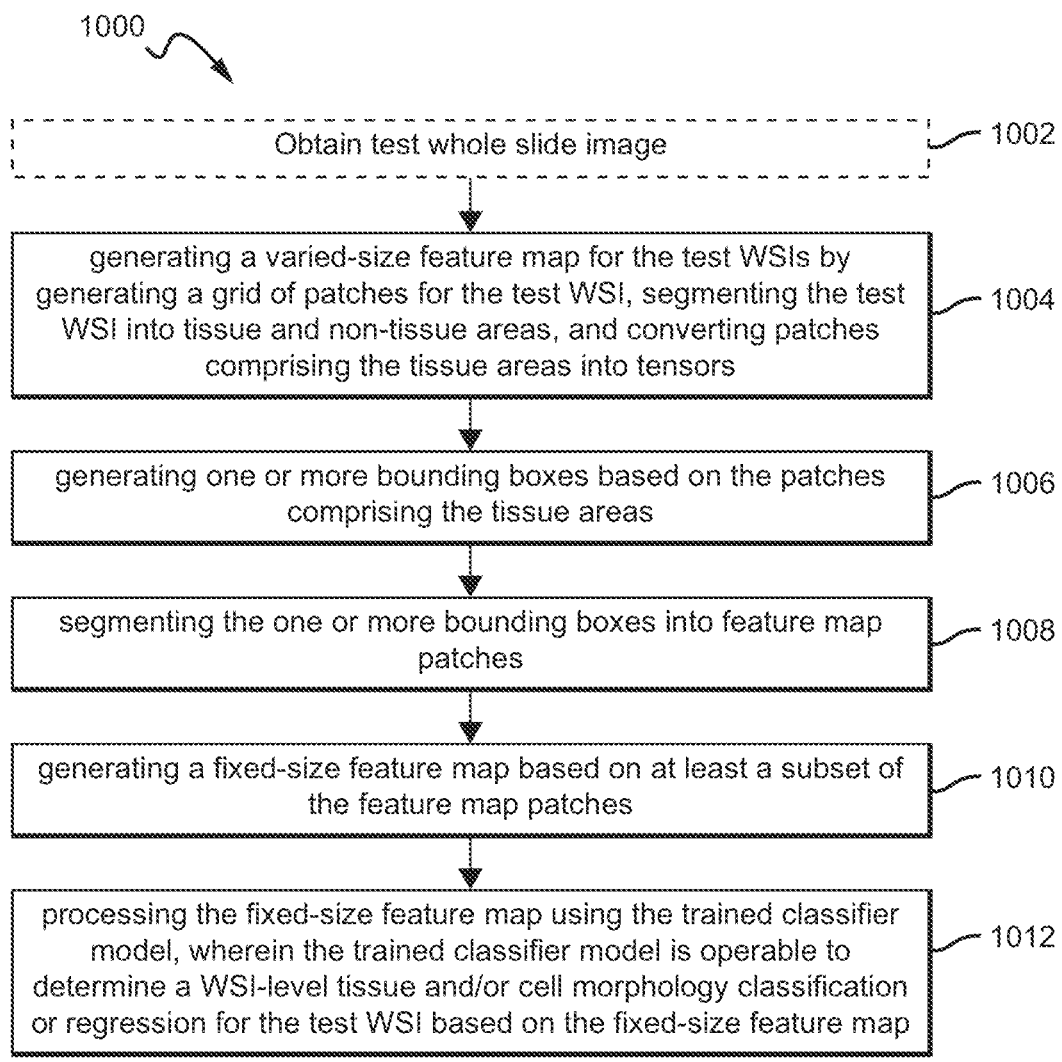
FIG. 10 illustrates a flow diagram of example operations for determining tissue or cell morphology classifications or regressions based on whole slide images in accordance with an embodiment.

FIG. 10 illustrates a flow diagram of example operations for determining tissue or cell morphology classifications or regressions based on whole slide images in accordance with an embodiment. In flow diagram 1000, a classification engine, e.g., classification engine 320, is configured to use the trained classifier model to determine a WSI-level tissue and/or cell morphology classification or regression for a test WSI. For example, a test WSI is obtained at step 1002. At step 1004, a varied-size feature map is generated for the test WSI by generating a grid of patches for the test WSI, segmenting the test WSI into tissue and non-tissue areas, and converting patches comprising the tissue areas into tensors. At step 1006, at least one bounding box is generated based on the patches comprising the tissue areas, and the at least one bounding box is segmented into feature map patches at step 1008. At step 1010, a fixed-size feature map is generated based on at least a subset of the feature map patches. The fixed-size feature map is processed using the trained classifier model at step 1012, wherein the trained classifier model is operable to determine a WSI-level tissue and/or cell morphology classification or regression for the test WSI based on the fixed-size feature map.

Test Results

Test results with respect to the various embodiments herein have been obtained based on 372 diagnostic (training) WSIs from lung adeno and squamous carcinoma cancer patients that were obtained from TCGA, LUAD, and LUSC sources and 152 test WSIs.

Figure 11A:
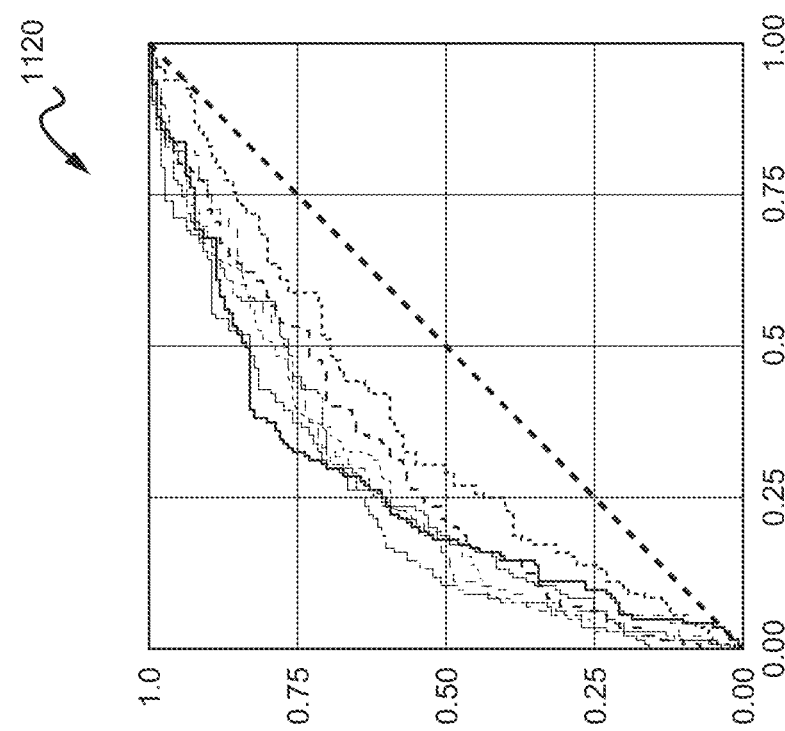
FIG. 11A illustrates a graphical representation of an AUC (Area Under the Curve)—ROC (Receiver Operating Characteristics) curve in accordance with an embodiment.
Figure 11B:
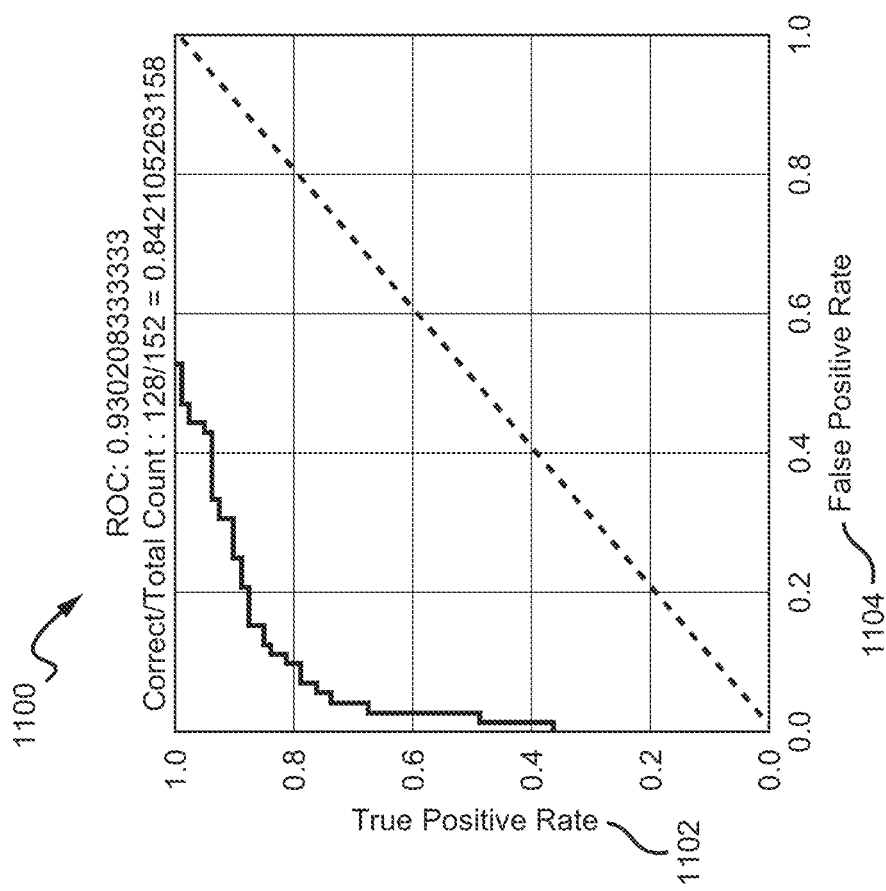
FIG. 11B illustrates a graphical representation of an AUC (Area Under the Curve)—ROC (Receiver Operating Characteristics) curve for a Stanford classifier.

FIG. 11A illustrates a graphical representation of an AUC (Area Under the Curve)—ROC (Receiver Operating Characteristics) curve in accordance with an embodiment. Plot 1100 is a graphical plot that illustrates the diagnostic ability of a trained classifier model, such as classifier model 508, as its discrimination threshold is varied. The true-positive rate 1102 is also known as sensitivity, recall or probability of detection in machine learning. The false-positive rate 1104 is also known as the fall-out or probability of false alarm and can be calculated as (1-specificity). Plot 1100 illustrates a relative operating characteristic (ROC) curve, plotting the sensitivity as a function of fall-out, that indicates an area under curve (AUC) of 0.93 AUC for the trained classifier model described herein. Moreover, the trained classifier model achieved a correct classification for 128 of the 152 test WSIs (84%). In comparison, FIG. 11B illustrates a graphical representation of an AUC (Area Under the Curve)—ROC (Receiver Operating Characteristics) curve for a Stanford classifier. Plot 1120 indicates that the AUC is for a Stanford classifier 0.75 versus the 0.93 for the trained classifier model described herein.

If a WSI-level label represents a regression (i.e., an estimation of continuous response (dependent) variables), the softmax+cross entropy loss classifier portion of the model may be replaced with a square residual loss function. Regression/continuous response labels may include, for example, a percentage of tumor-infiltrating lymphocytes, RNA expression, mutation burden, or allele frequency. In a further test using the dataset described above, the model including a square residual loss function rather than a softmax+cross entropy loss classifier was trained using training WSIs with PD-L1 gene expression labels, and the correlation between WSI and gene expression was ~0.4.

Thus, presented herein are systems and methods for determining tissue or cell morphology classifications or regressions based on pathology slide images. Traditionally, such classification has required using thousands or tens of thousands of images for training, however, the "weakly supervised" deep learning model herein can be trained for determining a tissue and/or cell morphology classification or regression using a limited amount of labeled training whole slide images and has been shown to achieve an overall concordance with correct classifications for 128 of 152 test WSIs.

Systems, apparatus, and methods described herein may be implemented using digital circuitry, or using one or more computers using well-known computer processors, memory units, storage devices, computer software, and other components. Typically, a computer includes a processor for executing instructions and one or more memories for storing instructions and data. A computer may also include, or be coupled to, one or more mass storage devices, such as one or more magnetic disks, internal hard disks and removable disks, magneto-optical disks, optical disks, etc.

Systems, apparatus, and methods described herein may be implemented using computers operating in a client-server relationship. Typically, in such a system, the client computers are located remotely from the server computers and interact via a network. The client-server relationship may be defined and controlled by computer programs running on the respective client and server computers.

A high-level block diagram of an exemplary client-server relationship that may be used to implement systems, apparatus and methods described herein is illustrated in FIG. 12. Client-server relationship 1200 comprises client 1210 in communication with server 1220 via network 1230 and illustrates one possible division of determining tissue or cell morphology classifications or regressions based on whole slide images between client 1210 and server 1220. For example, client 1210, in accordance with the various embodiments described above, may obtain and automatically upload training WSIs; optimally select a training dataset from the training WSIs; obtain and automatically upload a test WSI slide image; and receive a tissue and/or cell morphology classification or regression result. Server 1220 may obtain a plurality of training WSIs; generate a varied-size feature map for each of the plurality of training WSIs by generating a grid of patches for the training WSI, segmenting the training WSI into tissue and non-tissue areas, and converting patches comprising the tissue areas into tensors; generate at least one bounding box based on the patches comprising the tissue areas; segment the at least one bounding box into feature map patches; generate a fixed-size feature map based on at least a subset of the feature map patches; configure a classifier model to process fixed-size feature maps corresponding to the training WSIs such that, for each fixed-size feature map, the classifier model is operable to assign a WSI-level tissue and/or cell morphology classification or regression based on the tensors; train the classifier model using the fixed-size feature maps corresponding to the plurality of training WSIs; and configure a classification engine to use the trained classifier model to determine a WSI-level tissue and/or cell morphology classification or regression for a test WSI.

One skilled in the art will appreciate that the exemplary client-server relationship illustrated in FIG. 12 is only one of many client-server relationships that are possible for implementing the systems, apparatus, and methods described herein. As such, the client-server relationship illustrated in FIG. 12 should not, in any way, be construed as limiting. Examples of client devices 1210 can include cellular smartphones, kiosks, personal data assistants, tablets, robots, vehicles, web cameras, or other types of computing devices.

Systems, apparatus, and methods described herein may be implemented using a computer program product tangibly embodied in an information carrier, e.g., in a non-transitory machine-readable storage device, for execution by a programmable processor; and the method steps described herein, including one or more of the steps of FIGS. 9 and 10, may be implemented using one or more computer programs that are executable by such a processor. A computer program is a set of computer program instructions that can be used, directly or indirectly, in a computer to perform a certain activity or bring about a certain result. A computer program can be written in any form of programming language, including compiled or interpreted languages, and it can be deployed in any form, including as a stand-alone program or as a module, component, subroutine, or other unit suitable for use in a computing environment.

Figure 13:
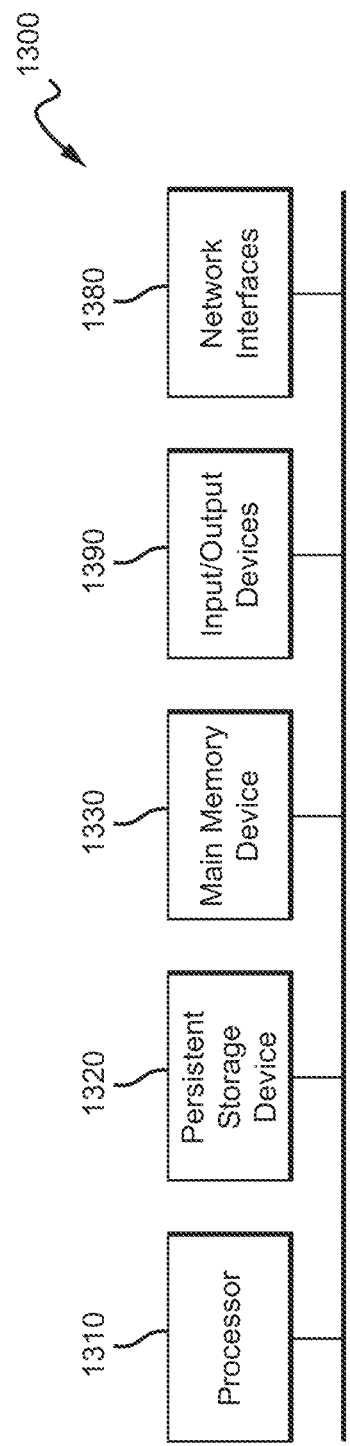
FIG. 13 illustrates a block diagram of a distributed computer system that can be used for implementing one or more aspects of the various embodiments.

A high-level block diagram of an exemplary apparatus that may be used to implement systems, apparatus and methods described herein is illustrated in FIG. 13. Apparatus 1300 comprises a processor 1310 operatively coupled to a persistent storage device 1320 and a main memory device 1330. Processor 1310 controls the overall operation of apparatus 1300 by executing computer program instructions that define such operations. The computer program instructions may be stored in persistent storage device 1320, or other computer-readable medium, and loaded into main memory device 1030 when execution of the computer program instructions is desired. For example, training engine 810 and classification engine 820 may comprise one or more components of computer 1300. Thus, the method steps of FIGS. 9 and 10 can be defined by the computer program instructions stored in main memory device 1330 and/or persistent storage device 1320 and controlled by processor 1310 executing the computer program instructions. For example, the computer program instructions can be implemented as computer executable code programmed by one skilled in the art to perform an algorithm defined by the method steps of FIGS. 9 and 10. Accordingly, by executing the computer program instructions, the processor 1310 executes an algorithm defined by the method steps of FIGS. 9 and 10. Apparatus 1300 also includes one or more network interfaces 1380 for communicating with other devices via a network. Apparatus 1300 may also include one or more input/output devices 1390 that enable user interaction with apparatus 1300 (e.g., display, keyboard, mouse, speakers, buttons, etc.).

Processor 1310 may include both general and special purpose microprocessors and may be the sole processor or one of multiple processors of apparatus 1300. Processor 1310 may comprise one or more central processing units (CPUs), and one or more graphics processing units (GPUs), which, for example, may work separately from and/or multi-task with one or more CPUs to accelerate processing, e.g., for various image processing applications described herein. Processor 1310, persistent storage device 1320, and/or main memory device 1330 may include, be supplemented by, or incorporated in, one or more application-specific integrated circuits (ASICs) and/or one or more field programmable gate arrays (FPGAs).

Persistent storage device 1320 and main memory device 1330 each comprise a tangible non-transitory computer readable storage medium. Persistent storage device 1320, and main memory device 1330, may each include high-speed random access memory, such as dynamic random access memory (DRAM), static random access memory (SRAM), double data rate synchronous dynamic random access memory (DDR RAM), or other random access solid state memory devices, and may include non-volatile memory, such as one or more magnetic disk storage devices such as internal hard disks and removable disks, magneto-optical disk storage devices, optical disk storage devices, flash memory devices, semiconductor memory devices, such as erasable programmable read-only memory (EPROM), electrically erasable programmable read-only memory (EEPROM), compact disc read-only memory (CD-ROM), digital versatile disc read-only memory (DVD-ROM) disks, or other non-volatile solid state storage devices.

Input/output devices 1390 may include peripherals, such as a printer, scanner, display screen, etc. For example, input/output devices 1390 may include a display device such as a cathode ray tube (CRT), plasma or liquid crystal display (LCD) monitor for displaying information (e.g., a DNA accessibility prediction result) to a user, a keyboard, and a pointing device such as a mouse or a trackball by which the user can provide input to apparatus 1300.

Any or all of the systems and apparatuses discussed herein, including training engine 810 and classification engine 820 may be performed by, and/or incorporated in, an apparatus such as apparatus 1300. Further, apparatus 1300 may utilize one or more neural networks or other deep-learning techniques to perform training engine 810 and classification engine 820 or other systems or apparatuses discussed herein.

One skilled in the art will recognize that an implementation of an actual computer or computer system may have other structures and may contain other components as well, and that FIG. 13 is a high-level representation of some of the components of such a computer for illustrative purposes.

The foregoing specification is to be understood as being in every respect illustrative and exemplary, but not restrictive, and the scope of the invention disclosed herein is not to be determined from the specification, but rather from the claims as interpreted according to the full breadth permitted by the patent laws. It is to be understood that the embodiments shown and described herein are only illustrative of the principles of the present invention and that various modifications may be implemented by those skilled in the art without departing from the scope and spirit of the invention. Those skilled in the art could implement various other feature combinations without departing from the scope and spirit of the invention.

We claim:

1. A computerized method of determining classifications based on whole slide images (WSIs), comprising:
    obtaining a plurality of training WSIs;
    generating a varied-size feature map for each of the plurality of training WSIs by generating patches for the training WSI, segmenting the training WSI into structured regions and non-structured regions, and converting the patches comprising structured regions into tensors;
    generating at least one bounding box based on the patches;
    segmenting the at least one bounding box into feature map patches;
    generating a fixed-size feature map based on at least a subset of the feature map patches;
    training a classifier model using the fixed-size feature maps, wherein the classifier model is configured to assign a WSI-level classification or regression based on the tensors; and
    configuring a classification engine to use the trained classifier model to determine a WSI-level structured region classification or regression for a test WSI.

2. The method of claim 1, wherein the plurality of training WSIs comprises less than 1000 WSIs.

3. The method of claim 1, wherein the plurality of training WSIs comprises hematoxylin and eosin (H&E)-stained whole slide images.

4. The method of claim 1, wherein each of the plurality of training WSIs corresponds to an WSI-level label indicating a structured region classification.

5. The method of claim 1, wherein each of the plurality of training WSIs corresponds to an WSI-level label indicating a regression.

6. The method of claim 1, further comprising converting patches of the grid of patches comprising non-structured regions into tensors comprising white feature components.

7. The method of claim 1, further comprising:
    filtering the grid of patches for a minimum color variance; and
    eliminating each patch determined to be empty space or background from further processing based on the filtering.

8. The method of claim 1, wherein each of the tensors comprises a multidimensional descriptive vector.

9. The method of claim 8, wherein the multidimensional descriptive vector comprises an RGB component.

10. The method of claim 1, further comprising converting the RGB component into a feature vector.

11. The method of claim 10, wherein the feature vector is a 512-feature vector for a resnet34 deep-learning neural network.

12. The method of claim 1, wherein each of the feature map patches comprises a fixed-size patch.

13. The method of claim 1, wherein the feature map patches comprise one of (16, 16, N) or (32, 32, N) tensors, and wherein N is a feature vector size.

14. The method of claim 1, further comprising generating the fixed-size feature map based on a randomly selected subset of the feature map patches.

15. The method of claim 1, wherein the subset of the feature map patches is arranged randomly within the fixed-size feature map.

16. The method of claim 1, further comprising selecting the subset of the feature map patches for further processing.

17. The method of claim 16, wherein the subset of the feature map patches is randomly selected.

18. The method of claim 16, wherein the subset of the feature map patches is selected to summarize content within a training WSI.

19. The method of claim 1, wherein the fixed-size feature map comprises one of a (256, 256, N) or (224, 224, N) feature map.

20. The method of claim 1, wherein the classifier model comprises a modified resnet34 deep-learning neural network.

21. The method of claim 1, wherein the classifier model comprises a two-layer convolutional deep-learning neural network.

22. The method of claim 1, wherein the classifier model comprises at least one of an Inception-v3, resnet34, resnet152, densenet169, densenet201 or other deep-learning neural network.

23. The method of claim 1, wherein each of the plurality of training WSIs corresponds to a different WSI.

24. The method of claim 1, further comprising:
obtaining the test WSI;
generating a varied-size feature map for the test WSIs by generating a grid of patches for the test WSI, segmenting the test WSI into structured and non-structured regions, and converting patches comprising the tissue areas into tensors;
generating at least one bounding box based on the patches comprising the structured regions;
segmenting the at least one bounding box into feature map patches;
generating a fixed-size feature map based on at least a subset of the feature map patches; and
processing the fixed-size feature map using the trained classifier model, wherein the trained classifier model is operable to determine a WSI-level structured region classification or regression for the test WSI based on the tensors.

25. An apparatus for determining classifications based on whole slide images (WSIs), the apparatus comprising:
a processor;
a memory device storing software instructions for determining molecular subtype classifications; and
a training engine executable on the processor according to software instructions stored in the memory device and configured to:
obtain a plurality of training WSIs;
generate a varied-size feature map for each of the plurality of training WSIs by generating patches for the training WSI, segmenting the training WSI into structured regions and non-structured regions, and converting the patches comprising structured regions into tensors;
generate at least one bounding box based on the patches;
segment the at least one bounding box into feature map patches;
generate a fixed-size feature map based on at least a subset of the feature map patches;
train a classifier model using the fixed-size feature maps, wherein the classifier model is configured to assign a WSI-level classification or regression based on the tensors; and
configure a classification engine to use the trained classifier model to determine a WSI-level structured region classification or regression for a test WSI.

26. A non-transitory computer-readable medium having computer instructions stored thereon for determining classifications based on whole slide images (WSIs), which, when executed by a processor, cause the processor to perform one or more steps comprising:
obtaining a plurality of training WSIs;
generating a varied-size feature map for each of the plurality of training WSIs by generating patches for the training WSI, segmenting the training WSI into structured regions and non-structured regions, and converting the patches comprising structured regions into tensors;
generating at least one bounding box based on the patches;
segmenting the at least one bounding box into feature map patches;
generating a fixed-size feature map based on at least a subset of the feature map patches;
training a classifier model using the fixed-size feature maps, wherein the classifier model is configured to assign a WSI-level classification or regression based on the tensors; and
configuring a classification engine to use the trained classifier model to determine a WSI-level structured region classification or regression for a test WSI.

27. An apparatus for determining classifications based on whole slide images (WSIs), the apparatus comprising:
a processor;
a memory device storing software instructions for determining tissue or cell morphology classifications or regressions; and
a classification engine executable on the processor according to software instructions stored in the memory device and configured to:
obtain a test WSI;
generate a varied-size feature map for the test WSI by generating a grid of patches for the test WSI, segmenting the test WSI into structured regions and non-structured regions, and converting patches comprising the tissue areas into tensors;
generate at least one bounding box based on the patches comprising the structured regions;
segment the at least one bounding box into feature map patches;
generate a fixed-size feature map based on at least a subset of the feature map patches; and determine a WSI-level structured region classification or regression for the test WSI using a classifier model trained to process the fixed-size feature map such that a WSI-level structured region classification or regression is determined based on the fixed-size feature map.

28. The apparatus of claim 27, wherein the classification engine comprises at least one of a cellular smartphone, kiosk, personal data assistant, tablet, robot, vehicle, web camera, or computing device.

* * * * *